US007932396B2

(12) United States Patent  (10) Patent No.: US 7,932,396 B2
Mansfield et al. (45) Date of Patent: *Apr. 26, 2011

(54) 2-PYRIDINYLCYCLOALKYLBENZAMIDE DERIVATIVES AND THEIR USE AS FUNGICIDES

(75) Inventors: Darren Mansfield, Bergisch Gladbach (DE); Pierre-Yves Coqueron, Lyons (FR); Heiko Rieck, Burscheid (DE); Philippe Desbordes, Lyons (FR); Alain Villier, Collonges au Mont d'Or (FR); Marie-Claire Grosjean-Cournoyer, Curis au Mont d'Or (FR); Pierre Genix, Lyons (FR)

(73) Assignee: Bayer Cropscience AG (DE)

( * ) Notice: Subject to any disclaimer, the term of this patent is extended or adjusted under 35 U.S.C. 154(b) by 187 days.

This patent is subject to a terminal disclaimer.

(21) Appl. No.: 11/920,216

(22) PCT Filed: May 17, 2006

(86) PCT No.: PCT/EP2006/062386
§ 371 (c)(1),
(2), (4) Date: Feb. 15, 2008

(87) PCT Pub. No.: WO2006/122952
PCT Pub. Date: Nov. 23, 2006

(65) Prior Publication Data
US 2009/0076096 A1 Mar. 19, 2009

(30) Foreign Application Priority Data

May 18, 2005 (EP) .................... 05356082

(51) Int. Cl.
A01N 43/40 (2006.01)
C07D 213/56 (2006.01)
(52) U.S. Cl. ...................... 546/337; 504/244
(58) Field of Classification Search .............. 546/337; 504/244
See application file for complete search history.

(56) References Cited

U.S. PATENT DOCUMENTS 7,524,968 B2 * 4/2009 Mansfield et al. .......... 546/345
7,687,067 B2 * 3/2010 Coqueron et al. .......... 424/405

FOREIGN PATENT DOCUMENTS

| WO | WO 9927783 | * | 6/1999 |
| WO | WO 99/42447 | | 8/1999 |
| WO | WO 01/11965 | | 2/2001 |
| WO | WO 2004/016088 | | 2/2004 |

OTHER PUBLICATIONS

Hcaplus 1970:530926, "Novel cyclization reactions of 2-(2-quinolyl)- or 2-(2-pyridyl) cyclohexanone oximes under conditions of Beckman rearrangement", 1970.*

Hcaplus 1999:372026, "Preparation of fungicidal acylated aminosalicylamides", Miesel et. al., 1999.*
Patani et. al., "Bioisosterism: A Rational Approach in Drug Design", Chem. Rev. 1996, 96, 3147-3176.*
Hcaplus 1970:530926, "Novel cyclization reactions of 2-(2-quinolyl)- or 2-(2-pyridyl) cyclohexanone oximes under conditions of Beckman rearrangement", 1970, Hamana et. al.*
Bourguignon, J. et al.: "Synthese D'Aryl Nitronorbornenes Par Cycloaddition De Diels-Alder Entre Les Aryl-Nitroethylenes Et Le Cyclopentadiene. Justification De La Stereochimie Et De La Reactivite Realtive Observees Far La Methode CNDO-II. Obtention D'Aryl Aminonorbornenes Synt", Canadian Journal of Chemistry, National Research Council, Ottawa, Canada, vol. 63, No. 9, 1985, pp. 2354-2361, XP009053818, ISSN: 0008-4042.
Hamana, M. et al.: "A Novel Cyclization Reactions of 2-(2-Quinolyl)- or 2-(2-Pyridy1)-Cyclohexanone Oximes Under Conditions of the Beckmann Rearragement" Yakugaku Zasshi—Journal of the Pharmaceutical Society of Japan, Nihon Yakugakkai, Tokyo, Japan, vol. 90, No. 8, 1970, pp. 991-1000, XP009053819, ISSN:0031-6903.
U.S. Appl. No. 11/587,908, filed Dec. 29, 2006, by Darren Mansfield, et al., entitled "2-Pyridinylcycloalkylbenzamide Derivatives and Their Use As Fungicides".
Notice of Allowance issued Jan. 2, 2009 in U.S. Appl. No. 11/587,908, filed Dec. 29, 2006, by Darren Mansfield et al. entitled "2-Pyridinylcycloalkylbenzamide Derivatives and Their Use As Fungicides".

* cited by examiner

Primary Examiner — Janet L Andres
Assistant Examiner — Heidi Reese
(74) Attorney, Agent, or Firm — Ostrolenk Faber LLP

(57) ABSTRACT

A compound of general formula (I):

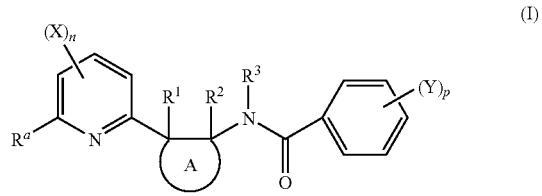

A process for preparing this compound.
A compound of general formula (II):

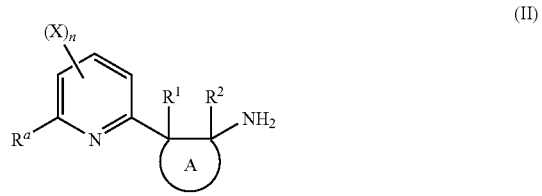

A fungicide composition comprising a compound of general formula (I).
A method for treating plants by applying a compound of general formula (I) or a composition comprising it.

13 Claims, No Drawings

2-PYRIDINYLCYCLOALKYLBENZAMIDE DERIVATIVES AND THEIR USE AS FUNGICIDES

CROSS-REFERENCE TO RELATED APPLICATION(S)

The present application is a 35 U.S.C. §371 national phase conversion of PCT/EP2006/062386 filed 17 May 2006, which claims priority of European Application No. 05356082.7 filed 18 May 2005.

The present invention relates to novel N-[2-(2-pyridinyl)cycloalkyl]benzamide derivatives, their process of preparation, their use as fungicides, particularly in the form of fungicidal compositions, and methods for the control of phytopathogenic fungi of plants using these compounds or their compositions.

International patent application WO 01/11965 discloses a broad family of fungicidal compounds. There is no specific disclosure of N-[2-(2-pyridinyl)cycloalkyl]benzamide derivatives.

It is always of high-interest in the field of agrochemicals to use pesticidal compounds more active than the compounds already known by the man ordinary skilled in the art whereby less compound can be used whilst retaining equivalent efficacy.

We have now found a new family of compounds which show enhanced fungicidal activity over the general known family of such compounds.

Accordingly, the present invention relates to a N-[2-(2-pyridinyl)cycloalkyl]benzamide derivative of general formula (I)

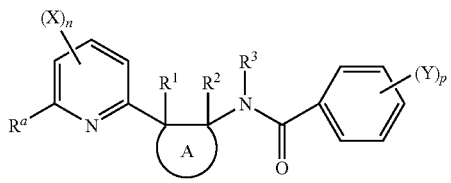

in which:

n is 1, 2, or 3;

p is 1, 2, 3, 4 or 5;

X is the same or different and is a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_3$-$C_8$-halogenoalkylcarbonyl having 1 to 5 halogen atoms, a $C_1$-$C_8$-alkylcarbamoyl, a di-$C_1$-$C_8$-alkylcarbamoyl, a (N—$C_1$-$C_8$-alkyl)oxycarbamoyl, a $C_1$-$C_8$-alkoxycarbamoyl, a (N—$C_1$-$C_8$-alkyl)-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkyl-sulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl or a phenylamino;

$R^a$ is a hydrogen atom, a halogen atom, a nitro group, a cyano group, a hydroxy group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkyl-sulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloximino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl or a phenylamino;

A is a 3-, 4-, 5-, 6- or 7-membered non aromatic carbocycle;

$R^1$ and $R^2$ are chosen, independently of each other, as being a hydrogen atom, a halogen atom, a cyano group, a hydroxy group, an amino group, a sulfnyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_6$-alkyl, a $C_2$-$C_6$-alkenyl, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkyl having 1 to 5 halogen atoms, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkenyloxy having 1 to 5 halogen atoms, a $C_3$-$C_6$-cycloalkyl, a $C_3$-$C_6$-halogenocycloalkyl having 1 to 5 halogen atoms, a $C_1$-$C_6$-alkylcarbonyl, a $C_1$-$C_6$-halogenoalkylcarbonyl having 1 to 5 halogen atoms, a $C_1$-$C_6$-alkylcarbamoyl, a di-$C_1$-$C_6$-alkylcarbamoyl, a N—$C_1$-$C_6$-alkyloxycarbamoyl, a $C_1$-$C_6$-alkoxycarbamoyl, a N—$C_1$-$C_6$-alkyl-$C_1$-$C_6$-alkoxycarbamoyl, a $C_1$-$C_6$-alkoxycarbonyl, a $C_1$-$C_6$-halogenoalkoxycarbonyl having 1 to 5 halogen atoms, a $C_1$-$C_6$-alkylcarbonyloxy, a $C_1$-$C_6$-halogenoalkylcarbonyloxy having 1 to 5 halogen atoms, a $C_1$-$C_6$-alkylcarbonylamino, a $C_1$-$C_6$-halogenoalkylcarbonylamino having 1 to 5 halogen atoms, a $C_1$-$C_6$-alkylaminocarbonyloxy, a di-$C_1$-$C_6$-alkylaminocarbonyloxy, a $C_1$-$C_6$-alkyloxycarbonyloxy, a $C_1$-$C_6$-alkylsulphenyl, a $C_1$-$C_6$-halogenoalkylsulphenyl having 1 to 5 halogen atoms, a $C_1$-$C_6$-alkylsulphinyl, a $C_1$-$C_6$-halogenoalkylsulphinyl having 1 to 5 halogen atoms, a $C_1$-$C_6$-alkylsulphonyl, a $C_1$-$C_6$-halogenoalkylsulphonyl having 1 to 5 halogen atoms, a benzyl, a benzyloxy, a benzylsulfanyl, a benzylsulfinyl, a benzylsulfonyl, a benzylamino, a phenoxy, a phenylsulfanyl, a phenylsulfinyl, a phenylsulfonyl, a phenylamino, a phenylcarbonylamino, a 2,6 dichlorophenyl-carbonylamino group or a phenyl group, $R^3$ is chosen as being a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_3$-$C_7$-cycloalkyl, a $C_3$-$C_7$-halogenocycloalkyl having 1 to 5 halogen atoms, a $C_3$-$C_7$-cycloalkyl-$C_1$-$C_6$-alkyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl or a $C_1$-$C_6$-halogenoalkylsulfonyl having 1 to 5 halogen atoms; and each substituent Y is chosen, independently of the others, as being a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms or a $C_1$-$C_8$-alkylsulfonamide;

as well as its salts, N-oxydes, metallic complexes, metalloidic complexes and optically active isomers.

In the context of the present invention:
halogen means fluorine, bromine, chlorine or iodine.
carboxy means —C(=O)OH; carbonyl means —C(=O)—; carbamoyl means —C(=O)NH$_2$; N-hydroxycarbamoyl means —C(=O)NHOH;

an alkyl group, an alkenyl group, and an alkynyl group as well as moieties containing these terms, can be linear or branched.

In the context of the present invention, it has also to be understood that in the case of di-substituted amino and of di-substituted carbamoyl radicals, the two substituents may form together with the nitrogen atom bearing them a saturated heterocyclic ring containing 3 to 7 atoms.

Any of the compound of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compound of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compound of general formula (I) wherein $R_1$ represents a hydroxy or sulfanyl group, and/or X represents a hydroxy, sulfanyl or amino group, may be found in its tautomeric form resulting of the shift of the proton of said hydroxy, sulfanyl or amino group. Such tautomeric forms of such compounds are also part of the present invention. More generally speaking, all tautomeric forms of compounds of general formula (I) wherein $R_1$ represents a hydroxy or sulfanyl group, and/or X represents a hydroxy, sulfanyl or amino group, as well as the tautomeric forms of the compounds which can optionally be used as intermediates in the preparation processes, and which will be defined in the description of these processes, are also part of the present invention.

According to the present invention, the 2-pyridyl is substituted in 6-position by $R^a$ and may be substituted in any other position by $(X)_n$, in which $R^a$, X and n are as defined above. Preferably, the present invention relates to N-[2-(2-pyridinyl)cycloalkyl]benzamide derivative of general formula (I) in which the different characteristics may be chosen alone or in combination as being:
as regards $R^a$, $R^a$ is a hydrogen atom or a halogen atom;
as regards n, n is 1 or 2;
as regards X, X is a halogen atom or a $C_1$-$C_8$-alkyl;
as regards the positions in which the 2-pyridyl moiety is substituted by X, the 2-pyridyl moiety is substituted by X in 3- and/or in 5-position.

According to the present invention, A is a 3-, 4-, 5-, 6- or 7-membered non aromatic carbocycle. Preferably, A is a 3-, 5-, 6- or 7-membered non aromatic carbocycle. Even more preferably, A is chosen from cyclopropyl, cyclopentyl, cyclohexyl and cycloheptyl.

According to the present invention, the phenyl group is substituted in any position by $(Y)_p$, in which Y and p are as defined above. Preferably, the present invention relates to N-[2-(2-pyridinyl)cycloalkyl]benzamide derivative of general formula (I) in which the different characteristics may be chosen alone or in combination as being:

as regards p, p is 1 or 2. More preferably p is 1;

as regards Y, Y is a hydrogen atom, a halogen atom, a $C_1$-$C_6$-alkyl, a $C_1$-$C_6$-alkoxy or a $C_1$-$C_6$-halogenoalkyl having 1 to 5 halogen atoms. More preferably, Y is halogen atom or a $C_1$-$C_6$-halogenoalkyl having 1 to 5 halogen atoms;

as regards the positions in which the phenyl moiety is substituted by Y, the phenyl moiety is substituted by Y preferentially first in ortho position.

According to the present invention, two of the carbon atoms of the cycloalkyl moiety of the compound of formula (I) are respectively substituted by $R^1$ and $R^2$. Preferably, the present invention also relates to N-[2-(2-pyridinyl)cycloalkyl]benzamide derivative of general formula (I) in which $R^1$ and $R^2$ may be chosen, independently of each other, as being a hydrogen atom, a halogen atom, a cyano group, a hydroxy group, a $C_1$-$C_6$-alkyl, a $C_1$-$C_6$-halogenoalkyl having 1 to 5 halogen atoms, a $C_2$-$C_6$-alkenyl, a $C_1$-$C_6$-alkoxy, a $C_1$-$C_6$-alkylsulfanyl, a $C_1$-$C_6$-alkylsulfenyl, a $C_1$-$C_6$-alkylsulfinyl, a $C_1$-$C_6$-alkoxycarbonyl, a $C_1$-$C_6$-alkylcarbonylamino, a $C_1$-$C_6$-alkoxycarbonyloxy, a $C_1$-$C_6$-alkoxycarbonylamino or a phenyl group. More preferably, $R^1$ and $R^2$ may be chosen, independently of each other, as being a hydrogen atom, a halogen atom, a $C_1$-$C_6$-alkyl, a $C_1$-$C_6$-halogenoalkyl having 1 to 5 halogen atoms or a $C_1$-$C_6$-alkylcarbonylamino. Even more preferably, $R^1$ and $R^2$ are both a hydrogen atom.

According to the present invention, the nitrogen atom of the carboxamide moiety of the compound of formula (I) is substituted by $R^3$, $R^3$ being as defined above. Preferably, the present invention also relates to N-[2-(2-pyridinyl)cycloalkyl]benzamide derivative of general formula (I) in which $R^3$ may be chosen as being a hydrogen atom or a $C_3$-$C_7$-cycloalkyl. Even more preferably, the $C_3$-$C_7$-cycloalkyl is cyclopropyl.

The present invention also relates to a process for the preparation of the compound of general formula (I). Thus, according to a further aspect of the present invention there is provided a process for the preparation of compound of general formula (I) as defined above, which comprises reacting a 2-pyridine derivative of general formula (II) or one of its salt:

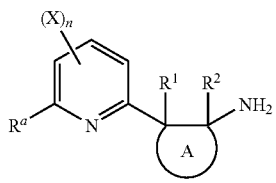

(II)

in which X, n, $R^a$, $R^1$, $R^2$ and A are as defined above;
with a carboxylic acid derivative of the general formula (III)

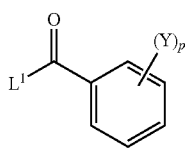

(III)

in which:
Y and p are as defined above; and
$L^1$ is a leaving group chosen as being a halogen atom, a hydroxyl group, —$OR^4$, —$OCOR^4$, $R^4$ being a $C_1$-$C_6$ alkyl, a $C_1$-$C_6$ haloalkyl, a benzyl, 4-methoxybenzyl, pentafluorophenyl or a group of formula

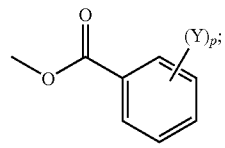

in the presence of a catalyst and, if $L^1$ is, a hydroxyl group, in the presence of a condensing agent.

The process according to the present invention is conducted in the presence of a catalyst. Suitable catalyst may be chosen as being 4-dimethyl-aminopyridine, 1-hydroxy-benzotriazole or dimethylformamide.

In case $L^1$ is a hydroxy group, the process according to the present invention is conducted in the presence of condensing agent. Suitable condensing agent may be chosen as being acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl-chloride; carbodiimides, such as N,N'-dicyclohexylcarbodiimide (DCC) or other customary condensing agents, such as phosphorous pentoxide, polyphosphoric acid, N,N'-carbonyldiimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromotripyrrolidino-phosphonium-hexafluorophosphate.

When $R^3$ is a hydrogen atom, the above mentioned process for the preparation of compound of general formula (I) may optionally be completed by a further step according to the following reaction scheme:

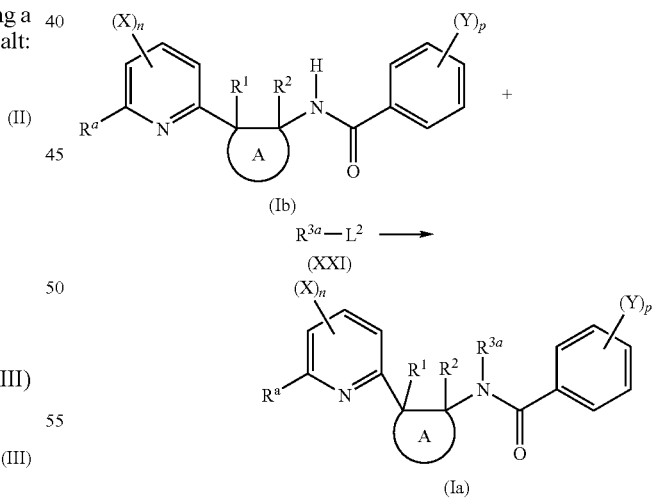

in which:
$R^1$, $R^2$, A, $R^a$, X, Y, n and p are as defined above;
$R^{3a}$ is chosen as being a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-halogenocycloalkyl having 1 to 5 halogen atoms, a $C_2$-$C_6$-alkenyl, a $C_2$-$C_6$-alkynyl, a $C_1$-$C_6$- alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenoalkylcarbonyl having 1 to 5 halogen atoms, a $C_1$-$C_6$-alkyloxycarbonyl, a $C_3$-$C_7$-cycloalkyl, a $C_3$-$C_7$-halogenocycloalkyl having 1 to 5 halogen atoms, a $C_3$-$C_7$-cycloalkyl-$C_1$-$C_6$-alkyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl or a $C_1$-$C_6$-halogenoalklylsulfonyl having 1 to 5 halogen atoms; and $L^2$ is a leaving group chosen as being a halogen atom, a 4-methyl phenylsulfonyloxy or a methylsulfonyloxy;

comprising the reaction of a compound of general formula (Ia) with a compound of general formula (XXI) to provide a compound of general formula (I).

Depending on the definition of A, $R^1$, $R^2$, $R^3$, amine derivatives of general formula (II) may be prepared by different processes. One example (a) of such a process may be when:
$R^1$, $R^2$, A, $R^a$, X, n are as defined above;
$R^3$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
then, the amine derivative of general formula (II) may be prepared according to a process comprising:
a first step according to reaction scheme a-1:

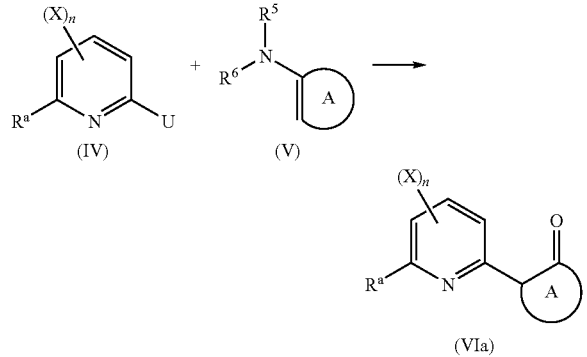

in which:
$R^1$, A, X and n are as defined above;
$R^5$ and $R^6$ are a $C_1$-$C_6$ alkyl or may form a 5-, 6- or 7-membered carbocyclic or heterocyclic ring;
U is a leaving group chosen as being a halogen, a $C_1$-$C_6$ alkylsulfonate or a $C_1$-$C_6$ haloalkylsulfonate;
comprising the arylation of an enamine derivative of general formula (V) by a pyridine derivative of general formula (IV), to provide a 2-(pyridyl)ketone derivative of general formula (VIa), at a temperature of from 0° C. to 200° C.;
a second step according to reaction scheme a-2:

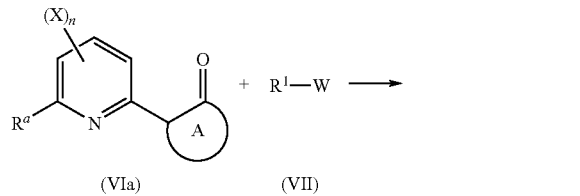

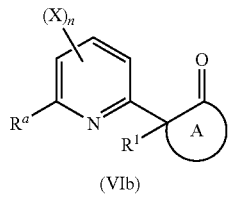

in which:
$R^a$, A, X and n are as defined above;
$R^1$ is a $C_1$-$C_6$ alkyl;
W is a halogen atom, a $C_1$-$C_6$ alkylsulfonate, a $C_1$-$C_6$ haloalkylsulfonate or a 4-methyl-phenylsulfonate,
comprising the alkylation of a compound of general formula (VIa) by a reagent of general formula (VII) to provide a compound of general formula (VIb);
a third step according to reaction scheme a-3:

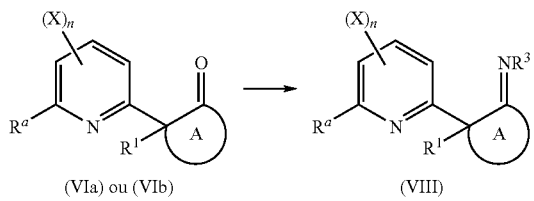

in which:
$R^a$, A, X and n are as defined above;
$R^1$ is a hydrogen atom or a $C_1$-$C_6$ alkyl;
$R^3$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
comprising the reaction of a compound of general formula (VIa) or (VIb) with an amine of formula $R^3$—NH2 to provide an imine derivative of general formula (VIII);
a fourth step according to scheme a-4:

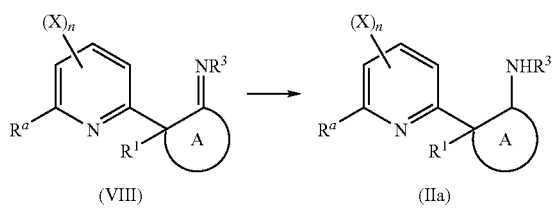

in which:
$R^a$, A, X and n are as defined above;
$R^1$ is a hydrogen atom, a $C_1$-$C_6$ alkyl,
$R^3$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
comprising the reduction of an imine derivative of general formula (VIII) by hydrogenation or by an hydride donor, in the same or a different pot to provide an amine derivative of general formula (IIa) or one of its salt.

A second example (b) of such a process may be when:
$R^1$, $R^2$, $R^3$, A, X and n are as defined above;
$R^1$ is a hydrogen atom;
then, the amine derivative of general formula (II) may be prepared according to a process comprising:

a first step according to reaction scheme b-1:

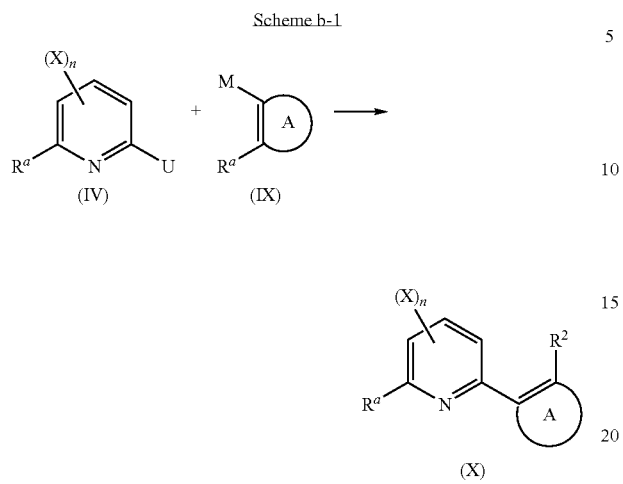

in which:

R$^a$, R$^2$, A, X and n are as defined above;

U is a leaving group chosen as being a halogen, a $C_1$-$C_6$ alkylsulfonate or a $C_1$-$C_6$ haloalkylsulfonate;

M is a metal or a metalloid specie;

comprising a coupling reaction of a pyridine derivative of general formula (IV) with a vinylic specie of general formula (IX), at a temperature of from 0° C. to 200° C., to provide a compound of general formula (X);

a second step according to reaction scheme b-2:

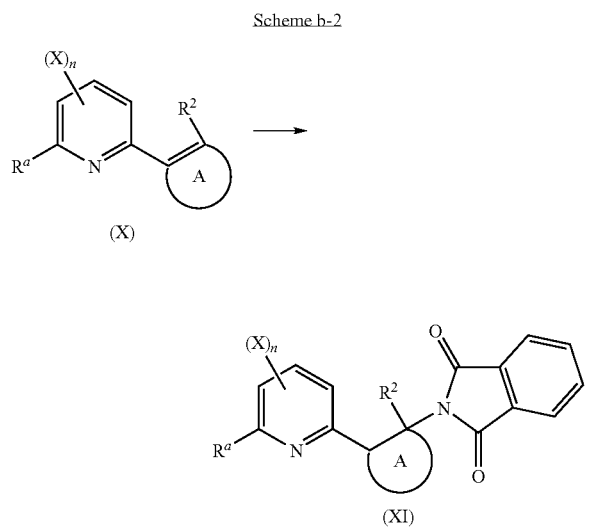

in which R$^a$, R$^2$, A, X and n are as defined above;

comprising the addition of a phtalimide or one of its salt on a compound of general formula (X) to provide a compound of general formula (XI);

a third step according to reaction scheme b-3:

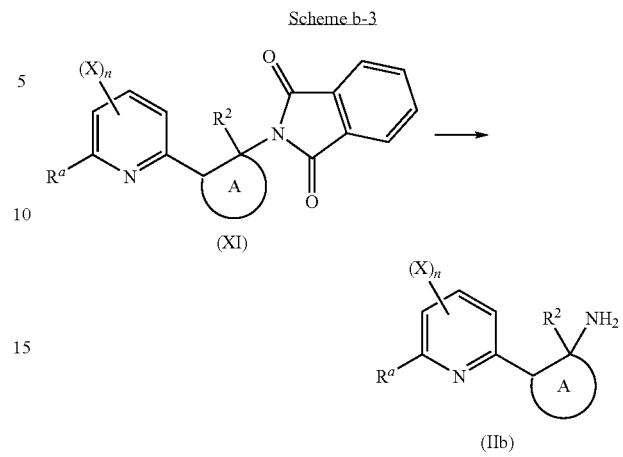

in which R$^a$, R$^2$, A, X and n are as defined above;

comprising the de-protection of a compound of general formula (XI) with hydrazine hydrate or an hydrazine salt, to provide an amine derivative of general formula (IIb) or one of its salts.

The first step (step b-1) of the process b according to the present invention is conducted in the presence of a vinylic specie of general formula (IX) in which M can be a metal or a metalloid specie. Preferably M is a tin derivative or a boron derivative. More preferably M is a tri-nbutyltin group.

The first step (step b-1) of the process b according to the present invention is conducted at a temperature of from 0° C. to 200° C.

The first step (step b-1) of the process b according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step b-1) of the process b according to the present invention may also be conducted in the presence of a catalyst Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(-)-1-[(S)-2-(dicyclohexylphosphino)ferrocenyl]ethyldicyclohexylphosphine and its corresponding enantiomer, or a mixture of both; (R)-(-)-1[(S)-2-(dicyclohexylphosphino)ferrocenyl]ethyldiphenylphosphine and its corresponding enantiomer, or a mixture of both; (R)-(-)-1[(S)-2-(diphenylphosphino)ferrocenyl]ethyldi-t-butylphosphine and its corresponding enantiomer, or a mixture of both; or (R)-(-)-1[(S)-2-(diphenylphosphino)ferrocenyl]ethyldicyclohexylphosphine and its corresponding enantiomer, or a mixture of both.

The first step (step b-1) of the process b according to the present invention may also be conducted in the presence of a base. Preferably, the base is chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

A third example (c) of such a process may be when:

R$^a$, R$^1$, X, n are as defined above;

R$^2$, R$^3$ are a hydrogen atom

A is a cyclopropyl ring;

then, the amine derivative of general formula (II) may be prepared according to a process comprising:

a first step according to reaction scheme c-1:

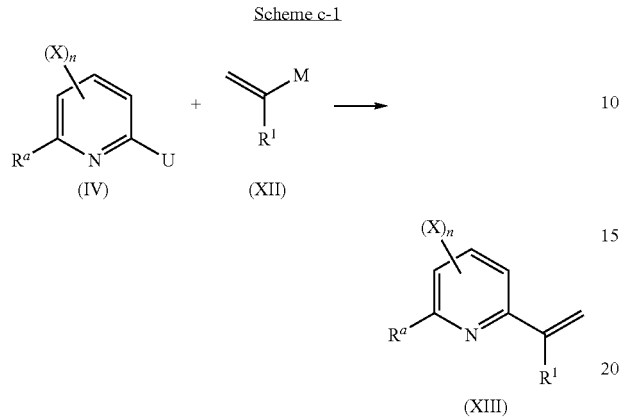

in which
R$^a$, R$^1$, X, n are as defined above;
U is a leaving group chosen as being a halogen, a C$_1$-C$_6$ alkylsulfonate or a C$_1$-C$_6$ haloalkylsulfonate;
M is a metal or a metalloid specie;

comprising a coupling reaction of a pyridine derivative of general formula (IV) with a vinylic specie of general formula (XII), at a temperature of from 0° C. to 200° C., to provide a compound of general formula (XIII);

a second step according to reaction scheme c-2:

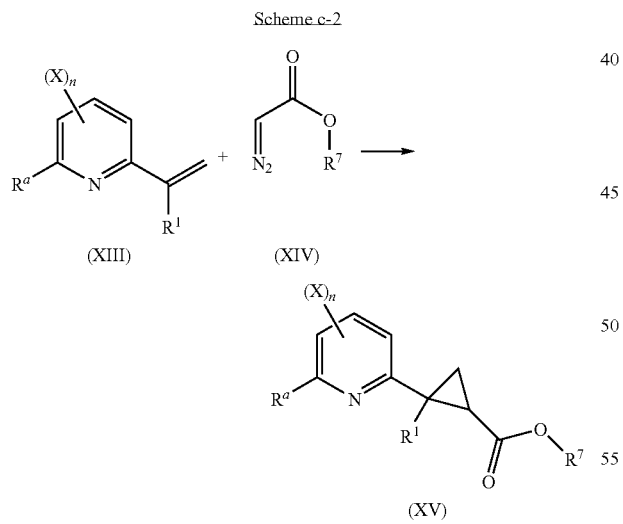

in which:
R$^a$, R$^1$, X and n are as defined above;
R$^7$ is a C$_1$-C$_6$ alkyl group;

comprising a cyclopropanation reaction of a vinylic pyridine derivative of general formula (XIII) with a diazo specie of general formula (XIV), at a temperature of from 0° C. to 200° C., to provide a compound of general formula (XV);

a third step according to reaction scheme c-3:

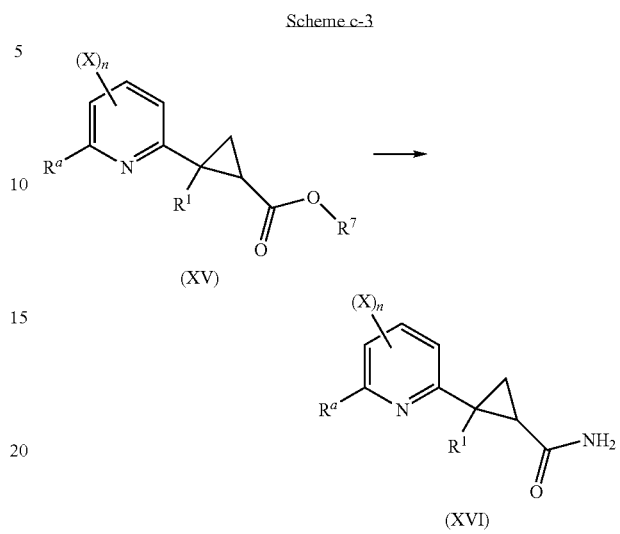

in which:
R$^a$, R$^1$, X and n are as defined above;
R$^7$ is a C$_1$-C$_6$ alkyl group;

comprising an amidification reaction of a ester derivative of general formula (XV) to provide a compound of general formula (XVI);

a fourth step according to reaction scheme c-4:

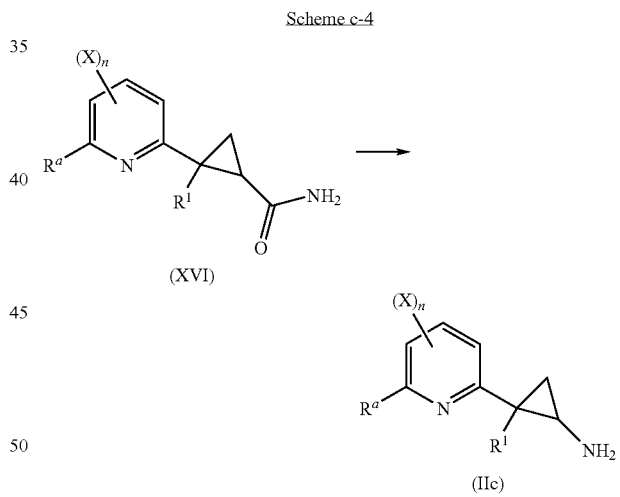

in which R$^a$, R$^1$, X and n are as defined above;
comprising a rearrangement reaction of a primary amide derivative of general formula (XVI) in presence of a halogenating agent, to provide an amine of general formula (IIc).

The first step (step c-1) of the process c according to the present invention is conducted in the presence of a vinylic specie of general formula (XII) in which M can be a metal or a metalloid specie. Preferably M is a tin derivative or a boron derivative. More preferably M is a tri-nbutyltin group.

The first step (step c-1) of the process c according to the present invention is conducted at a temperature of from 0° C. to 200° C.

The first step (step c-1) of the process c according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step c-1) of the process c according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(−)-1-[(S)-2-(dicyclohexylphosphino)ferrocenyl]ethyldicyclohexylphosphine and its corresponding enantiomer, or a mixture of both; (R)-(−)-1[(S)-2-(dicyclohexylphosphino)ferrocenyl]ethyldiphenylphosphine and its corresponding enantiomer, or a mixture of both; (R)-(−)-1[(S)-2-(diphenylphosphino)ferrocenyl]ethyldi-t-butylphosphine and its corresponding enantiomer, or a mixture of both; or (R)-(−)-1[(S)-2-(diphenylphosphino)ferrocenyl]ethyldicyclohexylphosphine and its corresponding enantiomer, or a mixture of both.

The first step (step c-1) of the process c according to the present invention may also be conducted in the presence of a base. Preferably, the base is chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

The present invention also relates to another process for the preparation of the compound of general formula (I). Thus, according to a further aspect of the present invention there is provided a process for the preparation of compound of general formula (I)

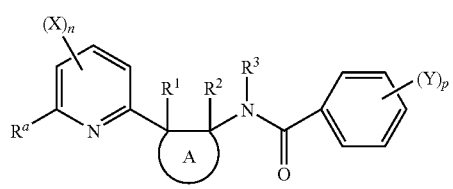

(I)

in which:
$R^a$, $R^1$, X, Y, n, p are as defined above;
$R^2$ and $R^3$ are a hydrogen atom; and
A is a cyclopropyl ring;
said process comprising:
a first step according to reaction scheme d-1

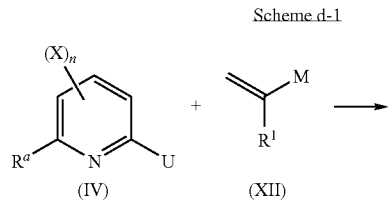

Scheme d-1

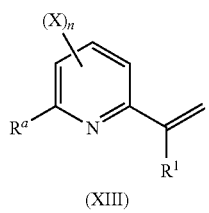

(XIII)

in which:
$R^a$, $R^1$, X, n are as defined above;
U is a leaving group chosen as being a halogen, a $C_1$-$C_6$ alkylsulfonate or a $C_1$-$C_6$ haloalkylsulfonate;
M is a metal or a metalloid specie; comprising a coupling reaction of a pyridine derivative of general formula (IV) with a vinylic specie of general formula (XII), at a temperature of from 0° C. to 200° C., to provide a compound of general formula (XIII);
a second step according to reaction scheme d-2:

Scheme d-2

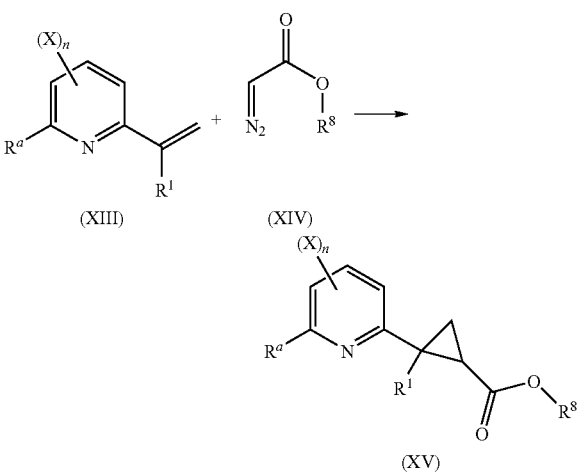

in which:
$R^a$, $R^1$, X and n are as defined above;
$R^8$ is a $C_1$-$C_6$ alkyl group;
comprising a cyclopropanation reaction of a vinylic pyridine derivative of general formula (XIII) with a diazo specie of general formula (XIV), at a temperature of from 0° C. to 200° C., to provide a compound of general formula (XV);
a third step according to reaction scheme d-3:

Scheme d-3

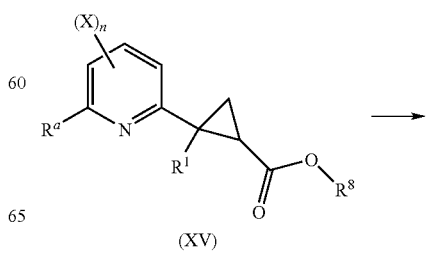

-continued

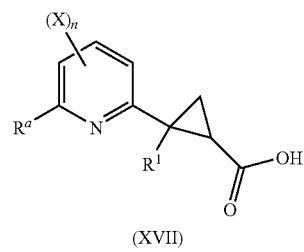

(XVII)

in which:
R$^a$, R$^1$, X and n are as defined above;
R$^8$ is a C$_1$-C$_6$ alkyl group;
comprising a hydrolysis reaction of an ester derivative of general formula (XV) to provide an acid of general formula (XVII);

a fourth step according to reaction scheme d-4:

Scheme d-4

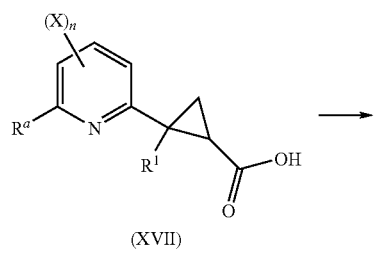

in which:
R$^a$, R$^1$, X and n are as defined above; and
R$^9$ is a C$_1$-C$_6$ alky, C$_1$-C$_6$ halogenoalkyl, a benzyl, an allyl, a methoxymethyl, 2-trimethylsilyl-ethyl group;
comprising a conversion of an acid derivative of general formula (XVII) into an isocyanate of general formula (XVIII) which is trapped in situ by an alcohol of general formula R$^9$—OH, to provide a carbamate of general formula (XIX);

a fifth step according to reaction scheme d-5:

Scheme d-5

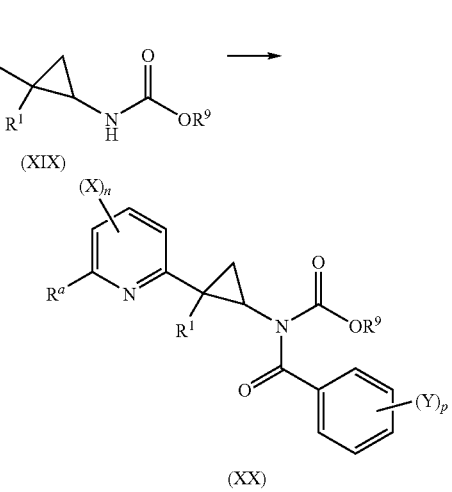

in which:
R$^a$, R$^1$, X, Y, n and p are as defined above; and
R$^9$ is a C$_1$-C$_6$ alkyl, C$_1$-C$_6$ halogenoalkyl, a benzyl, an allyl, a methoxymethyl, 2-trimethylsilyl-ethyl group;
comprising an acylation of a carbamate derivative of general formula (XIX) to provide a compound of general formula (XX);

a sixth step according to reaction scheme d-6:

Scheme d-6

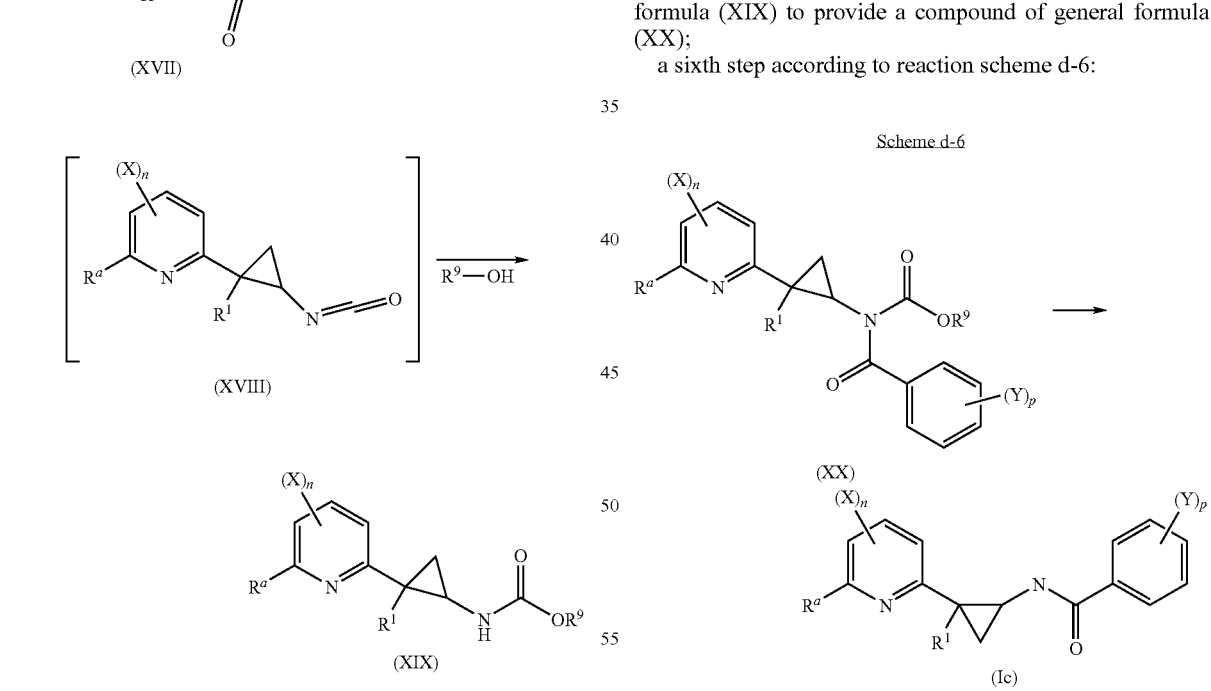

in which:
R$^a$, R$^1$, X, Y, n and p are as defined above; and
R$^9$ is a C$_1$-C$_6$ alkyl, C$_1$-C$_6$ halogenoalkyl, a benzyl, an allyl, a methoxymethyl, 2-trimethylsilyl-ethyl group;
comprising an de-protection of a carbamate derivative of general formula (XX) to provide a compound of general formula Ic;

The first step (step d-1) of the process c according to the present invention is conducted in the presence of a vinylic specie of general formula (XII) in which M can be a metal or a metalloid specie. Preferably M is a tin derivative or a boron derivative. More preferably M is a tri-nbutyltin group.

The first step (step d-1) of the process d according to the present invention is conducted at a temperature of from 0° C. to 200° C.

The first step (step d-1) of the process d according to the present invention may be conducted in the presence of a solvent. Preferably, the solvent is chosen as being water, an organic solvent or a mixture of both. Suitable organic solvents may for example be aliphatic, alicyclic or aromatic solvent The first step (step d-1) of the process c according to the present invention may also be conducted in the presence of a catalyst Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(−)-1-[(S)-2-(dicyclohexylphosphino)ferrocenyl]ethyldicyclohexylphosphine and its corresponding enantiomer, or a mixture of both; (R)-(−)-1[(S)-2-(dicyclohexylphosphino)ferrocenyl]ethyldiphenylphosphine and its corresponding enantiomer, or a mixture of both; (R)-(−)-1[(S)-2-(diphenylphosphino)ferrocenyl]ethyldi-t-butylphosphine and its corresponding enantiomer, or a mixture of both; or (R)-(−)-1[(S)-2-(diphenylphosphino)ferrocenyl]ethyldicyclohexylphosphine and its corresponding enantiomer, or a mixture of both.

The first step (step d-1) of the process c according to the present invention may also be conducted in the presence of a base. Preferably, the base is chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

The fourth step (step d-4) of the process d according to the present invention is conducted at a temperature of from −10° C. to 200° C.

The fourth step (step d-4) of the process d according to the present invention is conducted in the presence of a base. Preferably, the base is chosen as being an organic base. Suitable examples of such bases may for example be tertiary amines.

The fourth step (step d-4) of the process d according to the present invention is conducted in the presence of an azide donor. Preferably, the azide donor is chosen as being a phosphoryl azide. Suitable examples of such phosphoryl azides may for example be diphenylphosphoryl azide.

The fourth step (step d-4) of the process d according to the present invention is conducted in the presence of an alcohol. Preferably, the alcohol is chosen as being a $C_1$-$C_6$ alcohol. Suitable examples of such $C_1$-$C_6$ alcohol may for example be Tert-butanol.

The fifth step (step d-5) of the process d according to the present invention is conducted at a temperature of from −80° C. to 200° C.

The fifth step (step d-5) of the process d according to the present invention is conducted in the presence of a base. Preferably, the base is chosen as being an inorganic or an organic base. Suitable examples of such bases may for example be alkaline earth metal or alkali metal hydrides, hydroxides, amides, alcoholates, carbonates or hydrogen carbonates, acetates or tertiary amines. More preferably, the base is chosen as being alkaline earth metal, alkali metal hydrides or alkali metal alkides.

Compounds according to the present invention can be prepared according to the above described processes. It will nevertheless be understood that, on the basis of his general knowledge and of available publications, the skilled worker will be able to adapt these processes according to the specifics of each of the compounds which it is desired to synthesise.

The compound of general formula (II) used as an intermediate for the preparation of compound of general formula (I) is novel. Therefore, the present invention also relates to novel intermediate compound useful for the preparation of compound of general formula (I). Thus, according to the present invention, there is provided a compound of general formula (II):

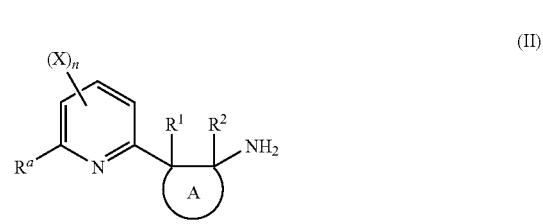

(II)

in which X, n, $R^a$, $R^1$, $R^2$ and A are as defined above.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amites, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous. Examples of suitable fungicide mixing partners may be selected in the following lists:

1) a compound capable to inhibit the nucleic acid synthesis like benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid;

2) a compound capable to inhibit the mitosis and cell division like benomyl, carbendazim, diethofencarb, ethaboxam, fuberidazole, pencycuron, thiabendazole thiophanate-methyl, zoxamide;

3) a compound capable to inhibit the respiration for example
as CI-respiration inhibitor like diflumetorim;
as CII-respiration inhibitor like boscalid, carboxin, fenfuram, flutolanil, furametpyr, furmecyclox, mepronil, oxycarboxine, penthiopyrad, thifluzamide;
as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

4) a compound capable of to act as an uncoupler like dinocap, fluazinam, meptyldinocap;

5) a compound capable to inhibit ATP production like fentin acetate, fentin chloride, fentin hydroxide, silthiofam;

6) a compound capable to inhibit AA and protein biosynthesis like andoprim, blasticidin-S, cyprodinil, kasugamycin, kasugamycin hydrochloride hydrate, mepanipyrim, pyrimethanil;

7) a compound capable to inhibit the signal transduction like fenpiclonil, fludioxonil, quinoxyfen;

8) a compound capable to inhibit lipid and membrane synthesis like biphenyl, chlozolinate, edifenphos, iodocarb, iprobenfos, iprodione, isoprothiolane, procymidone, propamocarb, propamocarb hydrochloride, pyrazophos, tolclofos-methyl, vinclozolin;

9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

10) a compound capable to inhibit cell wall synthesis like benthiavalicarb, bialaphos, dimethomorph, flumorph, iprovalicarb, polyoxins, polyoxorim, validamycin A;

11) a compound capable to inhibit melanine biosynthesis like carpropamid, diclocymet, fenoxanil, phthalide, pyroquilon, tricyclazole;

12) a compound capable to induce a host defence like acibenzolar-5-methyl, probenazole, tiadinil;

13) a compound capable to have a multisite action like Bordeaux mixture, captafol, captan, chlorthalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propineb, sulphur and sulphur preparations including calcium polysulphide, thiram, tolylfluanid, zineb, ziram;

14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl 1H-imidazole-1-carboxylate, 2-(4-chlorophenyl)-N-{2-[3-methoxy-4-(prop-2-yn-1-yloxy)phenyl]ethyl}-2-(prop-2-yn-1-yloxy)acetamide, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl) nicotinamide, 2-phenylphenol and salts, 3,4,5-trichloropyridine-2,6-dicarbonitrile, 3,4-dichloro-N-(2-cyanophenyl) isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidin-7-amine, 5-chloro-7-(4-methylpiperidin-1-yl)-6-(2,4,6-trifluorophenyl)[1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidin-7-amine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, methasulfocarb, methyl (2-chloro-5-{(1E)-N-[(6-methylpyridin-2-yl)methoxy] ethanimidoyl}benzyl)carbamate, methyl (2E)-2-{2-[({cyclopropyl[(4-methoxyphenyl)imino]methyl}thio) methyl]phenyl}-3-methoxyacrylate, methyl 1-(2,2- dimethyl-2,3-dihydro-1H-inden-1-yl)-1H-imidazole-5-carboxylate, methyl 3-(4-chlorophenyl)-3-{[N-(isopropoxycarbonyl)valyl]amino}propanoate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-N$^2$-(methylsulfonyl)valinamide, N-{(Z)-[(cyclopropylmethoxy)imino][6-(difluoromethoxy)-2,3-difluorophenyl]methyl}-2-phenylacetamide, N-{2-[3-chloro-5-(trifluoromethyl)pyridin-2-yl]ethyl}-2-(trifluoromethyl)benzamide, natamycin, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyrroInitrine, quintozene, tecloftalam, tecnazene, triazoxide, trichlamide and zarilamid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The fungicidal compositions of the present invention can be used to curatively or preventively control the phytopathogenic fungi of crops. Thus, according to a further aspect of the present invention, there is provided a method for curatively or preventively controlling the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the present invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., Actimidaceae sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the present invention, mention may be made of:

Powdery mildew diseases such as:

*Blumeria* diseases, caused for example by *Blumeria graminis*;

*Podosphaera* diseases, caused for example by *Podosphaera leucotricha*;

*Sphaerotheca* diseases, caused for example by *Sphaerotheca fuliginea*;

*Uncinula* diseases, caused for example by *Uncinula necator*;

Rust diseases such as:

*Gymnosporangium* diseases, caused for example by *Gymnosporangium sabinae*;

*Hemileia* diseases, caused for example by *Hemileia vastatrix*;

*Phakopsora* diseases, caused for example by *Phakopsora pachyrhizi* or *Phakopsora meibomiae*;

*Puccinia* diseases, caused for example by *Puccinia recondita*;

*Uromyces* diseases, caused for example by *Uromyces appendiculatus*;

Oomycete diseases such as:

*Bremia* diseases, caused for example by *Bremia lactucae*;

*Peronospora* diseases, caused for example by *Peronospora pisi* or *P. brassicae*;

*Phytophthora* diseases, caused for example by *Phytophthora infestans*;

*Plasmopara* diseases, caused for example by *Plasmopara viticola*;

*Pseudoperonospora* diseases, caused for example by *Pseudoperonospora humuli* or

*Pseudoperonospora cubensis*;

*Pythium* diseases, caused for example by *Pythium ultimum*;

Leafspot, leaf blotch and leaf blight diseases such as:

*Alternaria* diseases, caused for example by *Alternaria solani*;

*Cercospora* diseases, caused for example by *Cercospora beticola*;

*Cladiosporum* diseases, caused for example by *Cladiosporum cucumerinum*;

*Cochliobolus* diseases, caused for example by *Cochliobolus sativus*;

*Colletotrichum* diseases, caused for example by *Colletotrichum lindemuthanium*;

*Cycloconium* diseases, caused for example by *Cycloconium oleaginum;*
*Diaporthe* diseases, caused for example by *Diaporthe citri;*
*Elsinoe* diseases, caused for example by *Elsinoe fawcettii;*
*Gloeosporium* diseases, caused for example by *Gloeosporium laeticolor;*
*Glomerella* diseases, caused for example by *Glomerella cingulata;*
*Guignardia* diseases, caused for example by *Guignardia bidwelli;*
*Leptosphaeria* diseases, caused for example by *Leptosphaeria maculans; Leptosphaeria nodorum;*
*Magnaporthe* diseases, caused for example by *Magnaporthe grisea;*
*Mycosphaerella* diseases, caused for example by *Mycosphaerella graminicola; Mycosphaerella arachidicola; Mycosphaerella fijiensis;*
*Phaeosphaeria* diseases, caused for example by *Phaeosphaeria nodorum;*
*Pyrenophora* diseases, caused for example by *Pyrenophora teres;*
*Ramularia* diseases, caused for example by *Ramularia collo-cygni;*
*Rhynchosporium* diseases, caused for example by *Rhynchosporium secalis;*
*Septoria* diseases, caused for example by *Septoria apii* or *Septoria tycopercisi;*
*Typhula* diseases, caused for example by *Typhula incarnata;*
*Venturia* diseases, caused for example by *Venturia inaequalis;*
Root and stem diseases such as:
*Corticium* diseases, caused for example by *Corticium graminearum;*
*Fusarium* diseases, caused for example by *Fusarium oxysporum;*
*Gaeumannomyces* diseases, caused for example by *Gaeumannomyces graminis;*
*Rhizoctonia* diseases, caused for example by *Rhizoctonia solani;*
*Tapesia* diseases, caused for example by *Tapesia acuformis;*
*Thielaviopsis* diseases, caused for example by *Thielaviopsis basicola;*
Ear and panicle diseases such as:
*Alternaria* diseases, caused for example by *Alternaria* spp.;
*Aspergillus* diseases, caused for example by *Aspergillus flavus;*
*Cladosporium* diseases, caused for example by *Cladosporium* spp.;
*Claviceps* diseases, caused for example by *Claviceps purpurea;*
*Fusarium* diseases, caused for example by *Fusarium culmorum;*
*Gibberella* diseases, caused for example by *Gibberella zeae;*
*Monographella* diseases, caused for example by *Monographella nivalis;*
Smut and bunt diseases such as:
*Sphacelotheca* diseases, caused for example by *Sphacelotheca reiliana;*
*Tilletia* diseases, caused for example by *Tilletia caries;*
*Urocystis* diseases, caused for example by *Urocystis occulta;*
*Ustilago* diseases, caused for example by *Ustilago nuda;*
Fruit rot and mould diseases such as:
*Aspergillus* diseases, caused for example by *Aspergillus flavus;*
*Botrytis* diseases, caused for example by *Botiytis cinerea;*
*Penicillium* diseases, caused for example by *Penicillium expansum;*
*Sclerotinia* diseases, caused for example by *Scierotinia sclerotiorum;*
*Verticilium* diseases, caused for example by *Verticilium alboatrum;*
Seed and soilborne decay, mould, wilt, rot and damping-off diseases:
*Fusarium* diseases, caused for example by *Fusarium culmorum;*
*Phytophthora* diseases, caused for example by *Phytophthora cactorum;*
*Pythium* diseases, caused for example by *Pythium ultimum;*
*Rhizoctonia* diseases, caused for example by *Rhizoctonia solani;*
*Sclerotium* diseases, caused for example by *Sclerotium rolfsii;*
*Microdochium* diseases, caused for example by *Microdochium nivale;*
Canker, broom and dieback diseases such as:
*Nectria* diseases, caused for example by *Nectria galligena;*
Blight diseases such as:
*Monilinia* diseases, caused for example by *Monilinia laxa;*
Leaf blister or leaf curl diseases such as:
*Taphrina* diseases, caused for example by *Taphrina deformans;*
Decline diseases of wooden plants such as:
*Esca* diseases, caused for example by *Phaemoniella clamydospora;*
Diseases of flowers and Seeds such as:
*Botrytis* diseases, caused for example by *Botrytis cinerea;*
Diseases of tubers such as:
*Rhizoctonia* diseases, caused for example by *Rhizoctonia solani.*

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, *trichophyton* diseases and candidiases or diseases caused by *Aspergillus* spp., for example *Aspergillus fumigatus*.

The aspects of the present invention will now be illustrated with reference to the following tables of compounds and examples. The following Tables A to V illustrate in a non-limiting manner examples of fungicidal compounds according to the present invention. In the following Examples, M+1 (or M−1) means the molecular ion peak, plus or minus 1 a.m.u. (atomic mass units) respectively, as observed in mass spectroscopy.

Synthesis of 2-[3,5-dichloro-2-pyridinyl]cyclohexanamine hydrochloride 0.22 g (0.86 mmol) of 2-[3,5-dichloro-2-pyridinyl]cyclohexanone, 0.2 g of molecular sieves 3 Å, 0.53 g (6.85 mmol) of ammonium acetate are refluxed in 5 mL of methanol for 3 hours. Back at room temperature, 93 mg (0.018 mol) of sodium cyanoborohydride are added, the reaction mixture is refluxed for one hour and left overnight at room temperature. The medium is filtered, concentrated to dryness and 10 ml of aqueous sodium hydroxide 1M is added. The aqueous phase is extracted thrice with 10 ml of dichloromethane. The combined organic phases are washed twice with 10 ml of water, dried over magnesium sulfate, filtered and concentrated. 3 ml of a solution of hydrogen chloride in diethyl ether (1M) are added to the crude material. The precipitate is filtered and

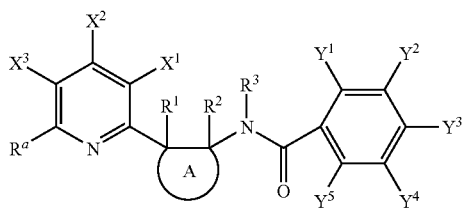

| Compound | $X^1$ | $X^2$ | $X^3$ | $R^1$ | $R^2$ | $R^3$ | $R^a$ | $Y^1$ | $Y^2$ | $Y^3$ | $Y^4$ | $Y^5$ | A | (M + 1) |
|---|---|---|---|---|---|---|---|---|---|---|---|---|---|---|
| 1 | Cl | H | Cl | H | H | H | H | $CF_3$ | H | H | H | H | Cyclohexyl | 417 |
| 2 | Cl | H | Cl | H | H | H | H | $CF_3$ | H | H | H | H | Trans-cyclopropyl | 375 |
| 3 | Cl | H | Cl | H | H | H | H | I | H | H | H | H | Trans-cyclopropyl | 433 |
| 4 | Cl | H | Cl | H | H | H | H | Me | H | H | H | H | Cyclopropyl | 321 |

EXAMPLES OF PROCESS FOR THE PREPARATION OF THE COMPOUND OF GENERAL FORMULA (I)

Example 1

Preparation of N-{2-[3,5-dichloro-2-pyridinyl]-cyclohexyl}-2-(trifluoromethyl)benzamide (Compound 1)

Preparation of 2-[3,5-dichloro-2-pyridinyl]cyclohexanone 5.00 g (0.030 mol) of 3,5-dichloro-2-fluoropyridine and 5.01 g of 1-(1-cyclohexen-1-yl)pyrrolidine (0.033 mol) are stirred neat together at room temperature for 1 h and are left at room temperature overnight. The reaction mixture is quenched with 40 ml of sulfuric acid 2M. Water is added to the reaction mixture (100 ml) which is extracted thrice with ethyl acetate (50 ml). The combined organic phases are washed with water (150 ml) and brine (100 ml). After separation, the organic phase is dried over magnesium sulfate filtered, concentrated to dryness and purified on silica gel to yield to 0.22 g of 2-[3,5-dichloro-2-pyridinyl]cyclohexanone (2%).

Mass spectrum: [M+1]=244 washed with diethyl ether to yield to 0.15 g of 2-[3-chloro-5-(trifluoromethyl)-2-pyridinyl]cyclohexanamine hydrochloride (56%).

Mass spectrum: [M+1-36]=245

Preparation of N-{2-[3,5-dichloro-2-pyridinyl]cyclohexyl}-2-(trifluoromethyl)benzamide (Compound 1)

0.70 g of 2-[3,5-dichloro-2-pyridinyl]cyclohexanamine hydrochloride (0.00022 mol), 0.07 ml of triethylamine, 49 mg (0.00023 mol) of 2-trifluoromethylbenzoyl chloride are stirred in 3 ml of dichloromethane at room temperature overnight. Dichloromethane is added (5 ml) to the reaction mixture, which is washed twice with water (5 ml). After separation, the organic phase is dried over magnesium sulfate, filtered, concentrated to dryness and purified on silica to yield to 32 mg of N-{2-[3,5-dichloro-2-pyridinyl]-cyclohexyl}-2-(trifluoromethyl)benzamide (31%).

Mass spectrum: M+1]=417

Example 2

Preparation of N-[2-(3,5-dichloropyridin-2-yl)cyclopropyl]-2-iodobenzamide (Compound 4)

Preparation of 3,5-dichloro-2-vinylpyridine 20.06 g of 3,5-dichloro-2-fluoropyridine (0.110 mol), 30.46 ml of tributyl-vinyl-stannane (0.103 mol), 6.00 g (0.00518 mol) of Pd(PPh$_3$)$_4$ are refluxed in 400 ml of toluene for five hours. The reaction mixture is washed thrice with a saturated aqueous solution of potassium fluoride 200 ml), once with water (300 ml), once with brine (300 ml). The combined aqueous phases are extracted with 100 ml of toluene. After separation, the combined organic phases are dried over magnesium sulfate, filtered, concentrated to dryness and purified on silica to yield to 15.05 g of 3,5-dichloro-2-vinylpyridine (62%) with 75% purity.

Mass spectrum: [M+1]=174.

Preparation of ethyl 2-(3,5-dichloropyridin-2-yl) cyclopropanecarboxylate

A mixture of 0.485 g of 3,5-dichloro-2-vinylpyridine (0.0014 mol) and 0.15 ml of ethyl diazoacetate (0.00127 mol) are added dropwise to 5 ml of refluxing xylene. The reaction mixture is refluxed for thirty minutes and left at room temperature overnight. After concentration to dryness and purification on silica, 250 mg of essentially pure ethyl 2-(3,5-dichloropyridin-2-yl)cyclopropanecarboxylate (75%) are obtained.

Mass spectrum: [M+1]=260

Preparation of 2-(3,5-dichloropyridin-2-yl)cylopropanecarboxylic acid 1.65 g of ethyl 2-(3,5-dichloropyridin-2-yl)cyclopropanecarboxylate (0.00634 mol) are dissolved in 20 ml of ethanol, 9.5 ml of sodium hydroxide 1M are added to the reaction mixture which is refluxed for 4 hours and left at room temperature overnight. After concentration in vacuo, 30 ml of water are added to the reaction mixture which is extracted twice with ethyl acetate (20 ml). The aqueous phase is acidified with HCl 1M. The precipitate which forms is filtered, air-dried to yield to 1.35 g of 2-(3,5-dichloropyridin-2-yl) cyclopropanecarboxylic acid (87%).

Mass spectrum: [M+1]=232.

Preparation of tert-butyl[2-(3,5-dichloropyridin-2-yl) cyclopropyl]carbamate 1.76 g of 2-(3,5-dichloropyridin-2-yl)cyclopropanecarboxylic acid (0.00758 mol), 1.17 ml of triethylamine (0.00834 mol), 2.50 g (0.00901 mol) of diphenyl-phosphoryl azide are refluxed for 4 hours in 25 ml of tert-butanol.

At room temperature, the reaction mixture is quenched with 100 ml of water and 10 ml of a solution of saturated sodium bicarbonate. After separation, the aqueous phase is extracted twice with 50 ml of ethyl acetate. The combined organic phases are dried over magnesium sulfate, filtered, concentrated to dryness and purified on silica to yield to 1.23 g of tert-butyl[2-(3,5-dichloropyridin-2-yl)cyclopropyl]carbamate (48%).

Mass spectrum: [M+1]=303

Preparation of tert-butyl[2-(3,5-dichloropyridin-2-yl) cyclopropyl](2-iodobenzoyl)carbamate Under argon, 0.50 g of tert-butyl[2-(3,5-dichloropyridin-2-yl)cyclopropyl]carbamate (0.00148 mol), are dissolved in 10 ml of tetrahydrofuran at −70° C. n-butyllithium (0.00226 mol) in solution in hexanes is added. After 5 minutes of stirring at −70° C., 0.46 g of 2-iodobenzoyl chloride (0.00166 mol) in solution in 50 ml of tetrahydrofuran are added dropwise. The reaction mixture is stirred at −70° C. for two hours and then allowed to room temperature overnight.

The reaction mixture is quenched with 50 ml of a solution of saturated ammonium chloride. After separation, the aqueous phase is extracted twice with 20 ml of ethyl acetate. The combined organic phases are dried over magnesium sulfate, filtered, concentrated to dryness and purified on silica to yield to 800 mg of 75% pure tert-butyl[2-(3,5-dichloropyridin-2-yl)cyclopropyl](2-iodobenzoyl)carbamate (74%).

Mass spectrum: [M+1]=533

Preparation of N-[2-(3,5-dichloropyridin-2-yl)cyclopropyl]-2-iodobenzamide (Compound 4)

0.800 g of tert-butyl[2-(3,5-dichloropyridin-2-yl)cyclopropyl](2-iodobenzoyl)carbamate (0.00075 mol) are dissolved in 7 ml of dichloromethane. 0.70 ml of trifluoroacetic acid are added to the reaction mixture which is left stirring at room temperature overnight. The reaction mixture is quenched with 15 ml of an aqueous solution of saturated sodium bicarbonate. After separation, the aqueous phase is extracted with dichloromethane (10 ml). The combined organic phases are dried over magnesium sulfate, filtered, concentrated to dryness and purified on silica to yield to 245 mg of N-[2-(3,5-dichloropyridin-2-yl)cyclopropyl]-2-iodobenzamide (65%).

Mass spectrum: [M+1]=433.

EXAMPLES OF BIOLOGICAL ACTIVITY OF THE COMPOUND OF GENERAL FORMULA (I)

Example A

In Vivo test on *Alternaria brassicae* (Leaf Spot of Crucifers)

The active ingredients tested are prepared by homogenization in a mixture of DMSO (dimethylsulfoxid)/acetone/tween/water. This suspension is then diluted with water to obtain the desired active material concentration.

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per cm$^3$). The spores are collected from a 12-13-day-old culture.

The contaminated radish plants are incubated for 6-7 days at about 18° C., under a humid atmosphere.

Grading is carried out 6 to 7 days after the contamination, in comparison with the control plants.

Under these conditions, good (at least 70%) to total protection is observed at a dose of 500 ppm with the following compounds: 1 and 3.

Example B

In Vivo Test on *Pyrenophora teres* (Barley Net Blotch)

The active ingredients tested are prepared by homogenization in a mixture of DMSO (dimethylsulfoxid)/acetone/tween/water. This suspension is then diluted with water to obtain the desired active material concentration.

Barley plants (Express or Plaisant variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Pyrenophor teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 70%) to total protection is observed at a dose of 500 ppm with the following compounds: 1, 3 and 4.

Example C

In Vivo Test on *Botrytis cinerea* (Gherkin Grey Mould)

The active ingredients tested are prepared by homogenization in a mixture of DMSO (dimethylsulfoxid)/acetone/tween/water. This suspension is then diluted with water to obtain the desired active material concentration.

Gherkin plants (Petit Vert de Paris variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatin
50 g/L of cane sugar
2 g/L of NH4NO3
1 g/L of KH2PO4

The contaminated gherkin plants are settled for 5/7 days in a climatic room at 15-11° C. (day/night) and at 80% relative humidity.

Grading is carried out 5/7 days after the contamination, in comparison with the control plants.

Under these conditions, good (at least 70%) or total protection is observed at a dose of 500 ppm with the following compounds: 3 and 4.

The N-{1-methylcarbamoyl-2-[3-chloro-5-(trifluoromethyl)-2-pyridinyl]-ethyl}-4-phenylbenzamide disclosed by Patent Application WO 01/11965 (see compound 316 in Table D) showed poor effectiveness on *Alternaria brassicae*, and zero effectiveness on *Botrytis cinerea* at 330 ppm; the N-{1-ethylcarbamoyl-2-[3-chloro-5-(trifluoromethyl)-2-pyridinyl]ethyl}-3-nitrobenzamide also disclosed by Patent Application WO 01/11965 (see compound 307 in Table D) showed poor effectiveness on *Alternaria brassicae* and zero effectiveness on *Botrytis cinerea* at 330 ppm; the N-{1-ethylcarbamoyl-2-[3-chloro-5-(trifluoromethyl)-2-pyridinyl]ethyl}-benzamide and the N-{1-methylcarbamoyl-2-[3-chloro-5-(trifluoromethyl)-2-pyridinyl]ethyl}-benzamide also disclosed by Patent Application WO 01/11965 (see compounds 304 and 314 in Table D) showed zero effectiveness on *Botrytis cinerea* at 330 ppm; and the N-{1-ethylcarbamoyl-2-[3-chloro-5-(trifluoromethyl)-2-pyridinyl]ethyl}-4-chlorobenzamide, the N-{1-ethylcarbamoyl-2-[3-chloro-5-(trifluoromethyl)-2-pyridinyl]ethyl}-2-bromobenzamide and the N-{1-methylcarbamoyl-2-[3-chloro-5-(trifluoromethyl)-2-pyridinyl]ethyl}-4-methoxybenzamide also disclosed by Patent Application WO 01/11965 (see compounds 306, 310 and 315 in Table D) showed zero effectiveness on *Botrytis cinerea* at 330 ppm.

The N-{[3-chloro-5-(trifluoromethyl)-2-pyridinyl]methyl}-5-thienylacetamide disclosed by Patent Application WO 01/11965 (see compound 101 in table B) showed poor efficacy against *Alternaria brassicae* and no efficacy against *Botpytis cinerea* and *Peronospora parasitica* at 330 ppm.

The invention claimed is:
1. A compound of general formula (I)

in which:

n is 1, 2, or 3;
p is 1, 2, 3, 4 or 5;
each X is independently selected from the group consisting of a halogen atom
$R^a$ is selected from the group consisting of a hydrogen atom, a halogen atom, a nitro group, a cyano group, a hydroxy group, a sulfanyl group, a pentafluoro-$\lambda^6$-sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_3$-alkynyl, a $C_1$-$C_8$-alkylamino, a di-$C_1$-$C_8$-alkylamino, a $C_1$-$C_8$ alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino;

A is a 3-, 4-, 5-, 6- or 7-membered non aromatic carbocycle;

$R^1$ and $R^2$ are independently selected from the group consisting of a hydrogen atom, a halogen atom, a cyano group, a hydroxy group, an amino group, a sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_6$-alkyl, a $C_2$-$C_6$-alkenyl, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkyl having 1 to 5 halogen atoms, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a $C_3$-$C_6$-cycloalkyl, a $C_3$-$C_6$-halogenocycloalkyl having 1 to 5 halogen atoms, a $C_1$-$C_6$-alkylcarbonyl, a $C_1$-$C_6$-halogenoalkylcarbonyl having 1 to 5 halogen atoms, a $C_1$-$C_6$-alkylcarbamoyl, a di-$C_1$-$C_6$-alkylcarbamoyl, a N—$C_1$-$C_6$-alkyloxycarbamoyl, a $C_1$-$C_6$-alkoxycarbamoyl, a N—$C_1$-$C_6$-alkyl-$C_1$-$C_6$-alkoxycarbamoyl, a $C_1$-$C_6$-alkoxycarbonyl, a $C_1$-$C_6$-halogenoalkoxycarbonyl having 1 to 5 halogen atoms, a $C_1$-$C_6$-alkylcarbonyloxy, a $C_1$-$C_6$-halogenoalkylcarbonyloxy having 1 to 5 halogen atoms, a $C_1$-$C_6$-alkylcarbonylamino, a $C_1$-$C_6$-halogenoalkylcarbonylamino having 1 to 5 halogen atoms, a $C_1$-$C_6$-alkylaminocarbonyloxy, a di-$C_1$-$C_6$-alkylaminocarbonyloxy, a $C_1$-$C_6$-alkyloxycarbonyloxy, a $C_1$-$C_6$-alkylsulfenyl, a $C_1$-$C_6$—halogenoalkylsulfenyl having 1 to 5 halogen atoms, a $C_1$-$C_6$-alkylsulfinyl, a $C_1$-$C_6$-halogenoalkylsulfinyl having 1 to 5 halogen atoms, a $C_1$-$C_6$-alkylsulfonyl, a $C_1$-$C_6$-halogenoalkylsulfonyl having 1 to 5 halogen atoms, a benzyl, a benzyloxy, a benzylsulfanyl, a benzylsulfinyl, a benzylsulfonyl, a benzylamino, a phenoxy, a phenylsulfanyl, a phenylsulfinyl, a phenylsulfonyl, a phenylamino, a phenylcarbonylamino, a 2,6 dichlorophenyl-carbonylamino group and a phenyl group, $R^3$ is selected from the group consisting of a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_3$-$C_7$-cycloalkyl, a $C_3$-$C_7$-halogenocycloalkyl having 1 to 5 halogen atoms, a $C_3$-$C_7$-cycloalkyl-$C_1$-$C_6$-alkyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl and a $C_1$-$C_6$-halogenoalkylsulfonyl having 1 to 5 halogen atoms; and each substituent Y is independently selected from the group consisting of a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms and a $C_1$-$C_8$-alkylsulfonamide;

or a salt, N-oxide, metallic complex, metalloidic complex or optically active isomer thereof.

2. The compound of claim 1 wherein $R^a$ is a hydrogen atom or a halogen atom.

3. The compound of claim 1 wherein n is 1 or 2.

4. The compound of claim 1 wherein the 2-pyridyl moiety is substituted by X in the 3- and/or in the 5-position.

5. The compound of claim 1 wherein A is selected from the group consisting of cyclopropyl, cyclopentyl, cyclohexyl and cycloheptyl.

6. The compound of claim 1 wherein p is 1 or 2.

7. The compound of claim 1 wherein Y is selected from the group consisting of a hydrogen atom, a halogen atom, a $C_1$-$C_6$-alkyl, a $C_1$-$C_6$-alkoxy and a $C_1$-$C_6$-halogenoalkyl having 1 to 5 halogen atoms.

8. The compound of claim 1 wherein the phenyl moiety is substituted by Y first in the ortho position.

9. The compound of claim 1 wherein $R^1$ and $R^2$ are independently selected from the group consisting of a hydrogen atom, a halogen atom, a cyano group, a hydroxy group, a $C_1$-$C_6$-alkyl, a $C_1$-$C_6$-halogenoalkyl having 1 to 5 halogen atoms, a $C_2$-$C_6$-alkenyl, a $C_1$-$C_6$-alkoxy, a $C_1$-$C_6$-alkylsulfanyl, a $C_1$-$C_6$-alkylsulfenyl, a $C_1$-$C_6$-alkylsulfinyl, a $C_1$-$C_6$-alkoxycarbonyl, a $C_1$-$C_6$-alkylcarbonylamino, a $C_1$-$C_6$-alkoxycarbonyloxy, a $C_1$-$C_6$-alkoxycarbonylamino and a phenyl group.

10. The compound of claim 1 wherein $R^3$ is selected from the group consisting of a hydrogen atom and a $C_3$-$C_7$-cycloalkyl.

11. A process for the preparation of compound of general formula (I) as defined in claim 1, which comprises reacting a 2-pyridine derivative of general formula (II) or one of its salts:

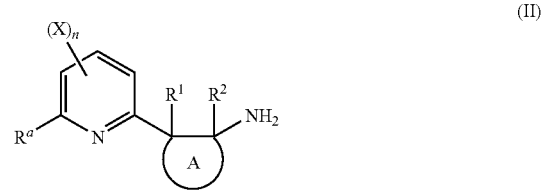

(II)

in which
each X is independently selected from the group consisting of a halogen atom;
n is 1, 2, or 3;
$R^a$ is selected from the group consisting of a hydrogen atom, a halogen atom, a nitro group, a cyano group, a hydroxy group, a sulfanyl group, a pentafluoro-$\lambda^6$-sulfanyl group, a N-hydroxycarbamoyl group, a carbamate group, a (hydroxyimino)-$C_1$-$C_6$-alkyl group, a $C_1$-$C_8$-alkyl, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino;

$R^1$ and $R^2$ are independently selected from the group consisting of a hydrogen atom, a halogen atom, a cyano group, a hydroxy group, an amino group, a sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_6$-alkyl, a $C_2$-$C_6$-alkenyl, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkyl having 1 to 5 halogen atoms, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a $C_3$-$C_6$-cycloalkyl, a $C_3$-$C_6$-halogenocycloalkyl having 1 to 5 halogen atoms, a $C_1$-$C_6$-alkylcarbonyl, a $C_1$-$C_6$-halogenoalkylcarbonyl having 1 to 5 halogen atoms, a $C_1$-$C_6$-alkylcarbamoyl, a di-$C_1$-$C_6$-alkylcarbamoyl, a N—$C_1$-$C_6$-alkyloxycarbamoyl, a $C_1$-$C_6$-alkoxycarbamoyl, a N—$C_1$-$C_6$-alkyl-$C_1$-$C_6$-alkoxycarbamoyl, a $C_1$-$C_6$-alkoxycarbonyl, a $C_1$-$C_6$-halogenoalkoxycarbonyl having 1 to 5 halogen atoms, a $C_1$-$C_6$-alkylcarbonyloxy, a $C_1$-$C_6$-halogenoalkylcarbonyloxy having 1 to 5 halogen atoms, a $C_1$-$C_6$-alkylcarbonylamino, a $C_1$-$C_6$-halogenoalkylcarbonylamino having 1 to 5 halogen atoms, a $C_1$-$C_6$-alkylaminocarbonyloxy, a di-$C_1$-$C_6$-alkylaminocarbonyloxy, a $C_1$-$C_6$-alkyloxycarbonyloxy, a $C_1$-$C_6$-alkylsulfenyl, a $C_1$-$C_6$-halogenoalkylsulfenyl having 1 to 5 halogen atoms, a $C_1$-$C_6$-alkylsulfinyl, a $C_1$-$C_6$-halogenoalkylsulfinyl having 1 to 5 halogen atoms, a $C_1$-$C_6$-alkylsulfonyl, a $C_1$-$C_6$-halogenoalkylsulfonyl having 1 to 5 halogen atoms, a benzyl, a benzyloxy, a benzylsulfanyl, a benzylsulfinyl, a benzylsulfonyl, a benzylamino, a phenoxy, a phenylsulfanyl, a phenylsulfinyl, a phenylsulfonyl, a phenylamino, a phenylcarbonylamino, a 2,6 dichlorophenyl-carbonylamino group and a phenyl group, and A is a 3-, 4-, 5-, 6- or 7-membered non aromatic carbocycle;

with a carboxylic acid derivative of the general formula (III)

$$\underset{L^1}{\overset{O}{\|}}{C}-\text{Ar}(Y)_p \quad (III)$$

in which:

each substituent Y is independently selected from the group consisting of a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms and a $C_1$-$C_8$-alkylsulfonamide;

p is 1, 2, 3, 4, or 5 and $L^1$ is a leaving group selected from the group consisting of a halogen atom, a hydroxyl group, —$OR^4$, —$OCOR^4$, $R^4$ being a $C_1$-$C_6$ alkyl, a $C_1$-$C_6$haloalkyl, a benzyl, 4-methoxybenzyl, pentafluorophenyl or a group of formula

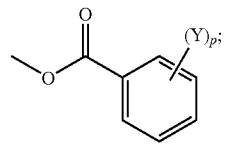

in the presence of a catalyst and, if $L^1$ is a hydroxyl group, in the presence of a condensing agent.

12. The process of claim 11 wherein $R^3$ is a hydrogen atom and the process is completed by a further step according to the following reaction scheme:

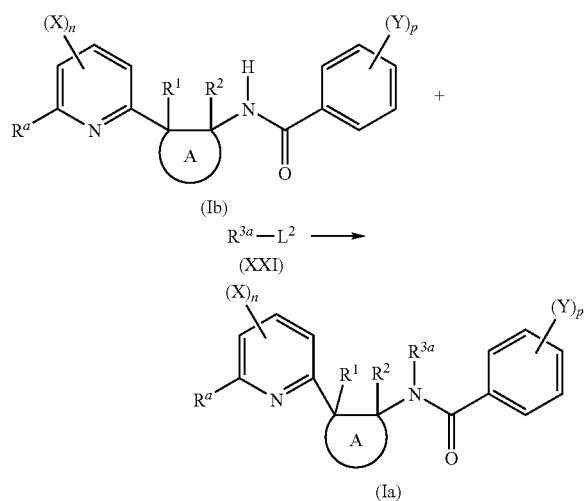

in which:

$R^{3a}$ is selected from the group consisting of a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_3$-$C_7$-cycloalkyl, a $C_3$-$C_7$-halogenocycloalkyl having 1 to 5 halogen atoms, a $C_3$-$C_7$-cycloalkyl-$C_1$-$C_6$-alkyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl and a $C_1$-$C_6$-halogenoalkylsulfonyl having 1 to 5 halogen atoms; and $L^2$ is a leaving group selected from the group consisting of a halogen atom, a 4-methyl phenylsulfonyloxy and a methylsulfonyloxy;

comprising reacting a compound of general formula (Ib) with a compound of general formula (XXI) to provide a compound of general formula (Ia).

13. A fungicide composition comprising an effective amount of a compound according to claim 1 and an agriculturally acceptable support.

* * * * *